United States Patent [19]
Balko

[11] Patent Number: 5,811,645
[45] Date of Patent: Sep. 22, 1998

[54] INBRED CORN LINE NP 2045

[75] Inventor: Larry G. Balko, Washington, Iowa

[73] Assignee: Novartis Finance Corporation, New York, N.Y.

[21] Appl. No.: 780,195

[22] Filed: Jan. 10, 1997

[51] Int. Cl.$^6$ .............................. A01H 5/00; A01H 4/00; A01H 1/00; C12N 5/04

[52] U.S. Cl. .................. 800/200; 800/250; 800/DIG. 56; 435/412; 435/424; 435/430; 435/430.1; 47/58; 47/DIG. 1

[58] Field of Search ...................................... 800/200, 205, 800/250, DIG. 56; 47/58, DIG. 1; 435/172.3, 172.1, 412, 424, 430, 430.1

[56] References Cited

PUBLICATIONS

Phillips et al. "Cell/Tissue Culture and Invitro Manipulation" In COrn and Corn Improvement, ASA Pub #18, 3rd edition p. 358, 1988.

*Primary Examiner*—Gary Benzion
*Attorney, Agent, or Firm*—Thomas Hoxie

[57] ABSTRACT

An inbred corn line, designated NP 2045, is disclosed. The invention relates to the seeds of inbred corn line NP 2045, to the plants of inbred corn line NP 2045 and to methods for producing a corn plant produced by crossing inbred line NP 2045 with itself or with another corn plant. The invention further relates to hybrid corn seeds and plants produced by crossing inbred line NP 2045 with another corn line.

16 Claims, No Drawings

INBRED CORN LINE NP 2045

BACKGROUND OF THE INVENTION

This invention relates to a new and distinctive corn inbred line designated NP 2045 and to hybrids made by using NP 2045 as a parent.

Corn (*Zea mays*) is a valuable and important field crop. Thus, plant breeders are continually developing new and superior corn inbred lines for production of high yielding, agronomically sound hybrids. The goal of the plant breeder is to combine in a single variety or hybrid an improved combination of desirable traits from the parent, inbred germplasm. These traits may include maximization of yield, resistance to disease and insects, tolerance to drought, heat and other environmental stresses. These traits are governed by a complex genetic system that makes selection and breeding of an inbred line challenging.

Corn hybrid development requires the development of homozygous inbred lines, the crossing of these lines, and the subsequent evaluation of those crosses. Pedigree, backcross, and recurrent selection breeding methods are used to develop inbred lines from breeding populations. Breeding programs combine the genetic backgrounds from two or more inbred lines or various other genetic sources into breeding pools from which new inbred lines are developed by self pollination and selection of desired phenotypes. The new inbred lines are crossed with other inbred lines, and hybrids from these crosses are evaluated to determine which have commercial potential.

Once the inbred parents that give a superior hybrid are identified, the hybrid seed can be reproduced indefinitely as long as inbred parent homogeneity is maintained. Corn hybrids may be either single cross hybrids, produced when two inbred lines are crossed to produce the first generation (F1) progeny; double cross hybrids, produced from four inbred lines crossed in pairs (A×B and C×D) and then the two F1 hybrids are crossed again (A×B)×(C×D); or three-way cross hybrids produced from crossing a single cross (A×B) to a third inbred line C. Numerous references are available on the topic of corn breeding and hybrid seed corn production. Those skilled in the art of corn breeding and production are well aware of techniques and methods for the development of inbred corn lines and corn hybrids. However, while many of the techniques and methods are known, breeder care and expertise must be used in the selection of breeding material for resulting yield increase and superior agronomic traits. Reference is made particularly to Corn and Corn Improvement, Third Edition, ed. G. F. Sprague and J. W. Dudley, American Society of Agronomy Monograph No. 18, particularly chapters 8 and 9, the substantive content of which is hereby incorporated by reference.

SUMMARY OF THE INVENTION

According to the invention, there is provided a novel inbred corn line, designated NP 2045. This invention thus relates to the seeds of inbred corn line NP 2045, to the plants of inbred corn line NP 2045 and to methods of producing a corn plant comprising the crossing of inbred line NP 2045 with itself or another corn line.

This invention further relates to hybrid corn seed produced by crossing the inbred line NP 2045 with another corn inbred line. More specifically the invention extends to hybrid corn seed produced by planting in pollinating proximity seeds of inbred corn line NP 2045 and a second inbred line having a genotype different from NP 2045; cultivating corn plants resulting from said planting until time of flowering; emasculating the flowers of plants of one of the inbred lines; allowing cross pollination to occur between the inbred lines; and harvesting seeds produced on the plants of the inbred line. The hybrid plants grown from the seed produced as stated above.

DEFINITIONS

In the description and examples that follow a number of terms are used; therefore, to provide a clear and consistent understanding of the specification and claims the following definitions are provided.

PRM=Predicted Relative Maturity. This trait is based on the harvest moisture of the grain. The relative maturity rating is based on a known set of checks, and is referred to as the Minnesota Relative Rating System.

MST=Harvest Moisture. The moisture is the actual percentage moisture of the grain at harvest.

YLD=Yield; bushels per acre. The actual yield of the grain at harvest (bu/a) adjusted to approximately 15.5% moisture.

$$HU = \text{Heat Units};$$

$$\frac{\text{Max Temp}(\leq 86° \text{ F.}) + \text{Min Temp}(\geq 50° \text{ F.})}{2} - 50$$

HUS=Heat units from emergence to 50% of plants in silk.

HU to pollen=Heat units from emergence to 50% of plants in pollen.

HU to pollen shed=Heat units from 10% to 90% pollen shed.

GRLS=Grey Leaf Spot.

BC1F1=(A×B)×B or A.

DETAILED DESCRIPTION OF THE INVENTION

Inbred corn line NP 2045 is a yellow dent inbred line with superior characteristics and is best suited as a male in crosses for production of first generation (F1) corn hybrids. NP 2045 is best adapted to the North central part of the United States. NP 2045 can be used to produce hybrids from approximately 110–120 PRM days based on the Minnesota Relative Maturity Rating System for harvest of grain. Inbred line NP 2045 has demonstrated good combining ability with families derived from Iowa Stiff Stalk, for example B73 and related lines LH119, LH132, W8304 (PVP Certificate No. 8800032) and Northrup King inbred line NP894.

Inbred corn line NP 2045 was derived from the crossing LH82, Holdens Foundation Seed, to Northrup King Co. Proprietary line NP J8606 (PVP Certificate No. 8900226). LH82×NPJ8606 was backcrossed to NPJ8606. Self-pollinations and selections were then practiced within the above BC1F1 hybrid cross for seven generations in the development of NP 2045. During the development of the line, crosses of segregating families were made to inbred testers to evaluate combining ability. Inbred line NP 2045 can be reproduced by planting seeds of the line, growing the resulting corn plants under self-pollination or sub-pollination conditions with adequate isolation and then harvesting the resulting seed. No variant traits have been observed or are expected in NP 2045.

The inbred fine has been evaluated at numerous research stations including stations across the Northern United States Corn Belt and Canada. Inbred line NP 2045 has shown uniformity and stability for all discernible characteristics as described in the following variety description. The description is based on data collected primarily at Washington, Iowa; Webster City, Iowa; and Napoleon, Ohio on 6 (six) replication in 1995. In interpreting the color designations herein, reference is made to the Munsell Glossy Book of Color, a standard color reference to describe all color choices.

TABLE 1

VARIETY DESCRIPTION INFORMATION FOR INBRED LINE NP 2045, Mo17 and NP 899 - UNITED STATES GEOGRAPHICAL AREAS

| | | NP 2045 | Mo17 | NP 899 |
|---|---|---|---|---|
| Type: | | Dent | Dent | Dent |
| Region Best Adapted: | | North central | Northern and Central | North Central |
| A. | Maturity: | | | |
| | HU to Silk (HUS): | 1361 (63 days) | 1510 (68 days) | 1408 (65 days) |
| | HU to pollen: | 1367 (63 days) | 1408 (64 days) | 1426 (65 days) |
| | HU to pollen shed: | 91 (3.3 days) | 98 (3.7 days) | 96 (3.7 days) |
| B. | Plant Characteristics: | | | |
| | Plant height (to tassel tip) (cm): | 196 | 226.7 | 227.1 |
| | Length to top ear internode (cm): | 14.5 | 15.6 | 16.4 |
| | Ear height (to base of top ear internode) (cm): | 59.6 | 82.2 | 80.4 |
| | Number of tillers: | 0 | 0 | 0 |
| | Number of ears per stalk: | 1 | 1 | 1 |
| | Cytoplasm type: | Normal | Normal | Normal |
| | Anthocyanin of brace roots: | Faint | Faint | Absent |
| C. | Leaf: | | | |
| | Color: | Medium green (7.5GY-4/2) | Medium green (7.5GY-4/2) | Medium green (7.5GY-4/4) |
| | Leaf angle (from 2nd leaf above ear at anthesis to stalk above leaf) | 16° | 33.5° | 32.5° |
| | Number of leaves- above top ear (mature plants): | 5.3 | 4.8 | 5.2 |
| | Marginal waves: (Scale: 1 = none to 9 = many): | 7 | 6 | 4.8 |
| | Width (widest point of ear node leaf) (cm): | 9 | 9.4 | 9.4 |
| | Sheath Pubescence: (Scale 0 = none to 9 = many): | 2 | 0 | 4.7 |
| | Longitudinal creases: (Scale: 1 = none to 9 = heavy): | 5 | 5 | 5 |
| | Length (ear node leaf) (cm): | 74.1 | 66.2 | 67.2 |
| D. | Tassel: | | | |
| | Number of primary lateral branches: | 7.3 | 5.5 | 11.2 |
| | Branch angle from central spike: | 33.7° | 54.7° | 49.2° |
| | Pollen shed: () = male sterile to 9 = heavy): | 7 | 5.8 | 7.7 |
| | Anther color: | Yellow (5Y-7/6) | Green-Yellow (2.5GY-8/6) | Purple (5RP-3/4) |
| | Glume color: | Light Green (5GY-6/6) | Light Green (5GY-5/6) | Green (7.5GY-5/6) |
| | Bar glumes: | Absent | Absent | Absent |
| | Tassel length (from top leaf collar to tassel tip): | 28.9 | 36.3 | 33.3 |

TABLE 1-continued

VARIETY DESCRIPTION INFORMATION FOR INBRED LINE NP 2045, Mo17 and NP 899 - UNITED STATES GEOGRAPHICAL AREAS

| | | NP 2045 | Mo17 | NP 899 |
|---|---|---|---|---|
| E. | Ear (Husked ear data except where stated otherwise): | | | |
| | Length (cm): | 12.9 | 18.6 | 15.5 |
| | Weight (gm): | 112.7 | 120.4 | 90.7 |
| | Midpoint diameter (mm): | 39.1 | 36.4 | 36.7 |
| | Kernel rows: | 15.6 | 10.6 | 14.8 |
| | Row alignment | Distinct Straight | Distinct Straight | Distinct Straight |
| | Silk color (3 days after emergence): | Green-yellow (2.5GY-8/6) | Green-yellow (2.5GY-8/6) | Pink (2.5R-7/6) |
| | Husk extension (length of the husk past the ear tip at maturity: | Medium <8 cm | Medium <8 cm | Medium <8 cm |
| | Taper of ear: | Slight | Slight | Average |
| | Husk color (fresh) 25 days after 50% silking: | Medium-green | Medium-green | Medium green |
| | Husk color (dry) 65 days after 50% silking: | Buff (2.5Y-8/4) | Buff (2.5Y-8/4) | Buff (2.5Y-8/4) |
| | Shank length (cm): | 10.8 | 11.9 | 7.9 |
| F. | Kernel (Dried): Size (from ear mid-point): | | | |
| | Length (mm): | 10.6 | 10.5 | 10.1 |
| | Width (mm): | 7.4 | 8.8 | 7.4 |
| | Thickness (mm): | 4.6 | 4.9 | 4.8 |
| | Shape grade (% of kernels that do not pass through a 13/64 slotted screen): | 65.2 | 48.7 | 57.8 |
| | Aleurone color: | Homozygous Bronze | Homozygous Bronze | Homozygous Yellow-orange |
| | Endosperm color: | Yellow-orange (7.5YR-5/8) | Yellow-orange (7.5YR-6/10) | Yellow-orange (7.5YR-6/10) |
| | Endosperm type: | Normal starch | Normal starch | Normal starch |
| | Gm weight/100 seeds (unsized): | 23.0 | 29.1 | 19.4 |
| G. | Cob: | | | |
| | Diameter at mid-point (mm): | 22.3 | 19.2 | 19.0 |
| | Color: | Red (10R-4/6) | Light red (10R-6/6) | White |
| H. | Agronomic Traits: | | | |
| | Stay Green: (At 65 days after anthesis), Scale 1 = worst to 9 = excellent): | 5.3 | 3 | 2 |
| | Kg/ha Yield on Inbred per se (At 12–13% grain moisture) | 4663 | 4585 | 3876 |
| I. | Disease Resistance: | | | |
| | Northern corn leaf blight: *Exserohilum turcicum* | 7 | 8 | 5 |
| | Grey leaf spot: *Cercospora zea-maydis* | 7 | 7 | 5 |
| | Southern leaf blight: *Bipolaris maydis*: | 4 | 6 | 3 |
| J. | Insect Resistance: European Corn Borer (*Ostrinia nubilialis*) | | | |
| | 1st generation | 5 | 7 | 6 |
| | 2nd generation | 6 | 5 | 2 |

The above disease and insect resistance description is based on a scale of 1–9; wherein 1–3 is considered susceptible, 4–5 intermediate, 6–7 resistant and 8–9 highly resistant.

With respect to publicly available inbred lines, NP 2045 most closely resembles Mo17. However, these lines differ in a number of characteristics. The lines differ in plant height, ear height, ear length and number of kernel rows. While NP 2045 is shorter than Mo17 and has lower ear height, it has more kernel rows compared to Mo17. Other characteristics between NP 2045 and Mo17 are summarized in Table 1.

NP 2045 most closely resembles Northrup King inbred line NP 899 (PVP Certificate No. 9400106) in terms of usage and maturity. Line NP 899 is claimed in U.S. Pat. No. 5,530,181 and has ATCC accession No. 97362. However, the following quantitative traits are statistically differentiating (TABLE 2).

TABLE 2

| Characteristic | NP 2045 | NP 899 | Sample Size | Standard Deviation |
|---|---|---|---|---|
| 1. Plant Height (cm): | 196.0 | 227.1 | 30 | 2.74 |
| 2. Ear Height (cm): | 59.6 | 80.4 | 30 | 5.84 |
| 3. Anther Color: | Yellow (5Y-7/6) | Purple (5RP-3/4) | | |

These data were taken from Washington, Iowa; Webster City, Iowa; and Napoleon, Ohio on 6 replications in 1995.

In addition to phenotypic observations, the genotype of a plant can also be examined. There are many techniques available for the analysis, comparison and characterization of plant genotype and these include isozyme electrophoresis, restriction fragment length polymorphism (RFLPs), randomly amplified polymorphic DNAs (RAPDs) sequence characterized amplified regions (SCARs) and amplified fragment length polymorphisms (AFLPs). While many of the techniques are used, RFLPs have the advantage of revealing an exceptionally high degree of allelic variation in corn. Moreover, there are a tremendous number of markers available to use. Reference is made to Mumm and Dudley, A classification of 148 U.S. Maize Inbreds: I Cluster Analysis Based on RFLP's, Crop Sci., 34:842–851 (1994), and Lee, M "Inbred Lines of Maize and Their Molecular Markers" The Maize Handbook (Springer-Verlag, New York, Inc. 1994 which are hereby incorporated by reference.

Both inbred lines NP 2045 and Mo17 were subject to various RFLP probes and the results indicate that the two inbreds have 55 out of 107 loci with different alleles. Additional RFLP relationship data indicates that NP 2045 is different from NP 899.

This invention is also directed to methods for producing a corn plant by crossing a first parent corn plant with a second parent corn plant, wherein the first or second corn plant is a corn plant of the inbred line NP 2045. However, both first and second parent corn plant can come from the inbred corn line NP 2045. Therefore, any methods using NP 2045 are part of this invention including self-pollination, backcross-pollination, hybrid breeding and crosses to produce germplasm populations.

It may be desirable to use a male-sterile (either cytoplasmic or nuclear) female parent to prevent self-pollination. If the female is not male-sterile, then either physical or chemical steps may be taken to ensure that self-pollination does not occur.

Any plants produced using inbred corn line NP 2045 as a parent are within the scope of this invention including any plant produced by the use of cells, protoplasts or tissue from NP 2045.

Specifically, NP 2045 produces hybrids that are competitive yielding, have good stalk strength, stay green ratings and Grey Leaf Spot resistance.

The techniques used to obtain the corn hybrid seeds and plants of this invention are conventional in the seed industry and are well known to those skilled in the art. The two parent lines are planted in pollinating proximity to each other in alternating sets of rows; however, any convenient planting pattern that allows for the free transfer of pollen is acceptable. The plants of both inbred lines are allowed to grow until the time of flowering. At flowering, tassels are removed from all plants of the female parent by hand, machine or other means. Natural cross-pollination is allowed to occur. Ears from the female plants are harvested to obtain novel F1 hybrid corn seeds of the present invention. F1 hybrid corn plants of the invention are obtained by planting seeds harvested from the female plant.

An example of a competitive yielding hybrid of this invention is that produced by the cross Northrup King Co. Inbred line NP 894×NP 2045 The hybrid produced from NP 894×NP 2045 is a 115 Minnesota Relative Maturity (RM) single cross hybrid. This hybrid most closely resembles the commercially available Northrup King Co. hybrid N6223, N6822 and N6330.

The hybrid produced by the cross NP 894×NP 2045 has significantly better Grey Leaf Spot resistance compared to N6223 and Pioneer (P) 3489 (Table 3). Table 3 also shows data for NP 894×NP 2045 compared to N6822, N6330 and Pioneer (P) 3394. NP 894×NP 2045 is also significantly higher for yield and Grey Leaf Spot resistance compared to N6330, N6822 and P3394.

TABLE 3

Combined Location and Year Performance Data
(1995, 1996; 72 environments; 110–120 RM Markets)

| Hybrid | YLD (bu/a) | MST (%) | GRLS |
|---|---|---|---|
| NP 894 × NP 2045 | 156.1 | 19.8 | 3.3 |
| N6223 | 152.8 | 18.0 | 6.0 |
| N6330 | 149.3 | 18.8 | 5.6 |
| N6822 | 150.7 | 19.3 | 6.6 |
| P3394 | 151.4 | 18.4 | 7.5 |
| P3489 | 154.3 | 18.6 | 5.1 |
| Trials with data: | 72 | 72 | 9 |
| LSD | 4.3 | 0.3 | 0.9 |

GRLS = Grey Leaf Spot, a rating to 1 = best resistance, 9 = most susceptible.

As used herein the term plant includes plant cells, plant protoplasts, plant cell tissue cultures including that from which corn plants fertile or otherwise can be regenerated, plant calli and plant cell clumps, and differentiated forms of plants such as, but not limited to embryos, pollen, stamen, anthers, flowers, kernels, ears, cobs, leaves, stalks, roots, shoots, plantlets, silks and kernels. In this context, the invention also includes a corn plant regenerated from any NP 2045 corn cell, protoplast and tissue mentioned above and having the same genotype as NP 2045.

Methods of cell and tissue culture and regeneration are well known in the art and described for example in "Plant Tissue Culture Manual: Fundamentals and Application", Ed. K. Lindsey, Kluwer (1991) and in Green and Rhodes, "Plant Regeneration in Tissue Culture of Maize", Maize for Biological Research (Plant Molecular Biology Association, Charlottesville, Va., 1982, pp. 367–372), which are hereby incorporated by reference.

As is well known, corn can be put to a wide variety of uses not only as livestock feed but also for human consumption of corn kernels and as a raw material in industry. Both grain and non-grain portions of the plant are used as a livestock feed for swine, cattle and poultry. In the food industry corn is used in wet and dry milling. In wet milling there is the separation of the germ, hull gluten and starch. Germ is used to produce corn oil and germ cake for feed. Corn starch may be packaged for human consumption or used in food products such as sauces, gravies, puddings, sweeteners, syrups, and baking powder. Other nonedible uses include textiles, paper, adhesives, cosmetics, explosives, corn binders, laundry purposes and agricultural formulations. Dry milling is used to produce breakfast foods, grits, cornmeal and corn flour. Other uses of corn include fuel, in the form of fuel alcohol or ethanol; seed; alcoholic beverages and construction.

DEPOSIT INFORMATION

Deposits of at least 2500 seeds of inbred NP 2045, has been made unrestrictedly available to the public via the American Type Culture Collection (ATCC), Rockville, Md. 20852 USA. The deposit corresponds to ATCC Deposit No. 209450, ATCC and was made on Nov. 12, 1997. The seeds are from stock maintained by Northrup King since prior to filing this application or any parents thereof. The deposit of inbred corn line NP 2045 will be maintained in the ATCC depository, which is a public depositary, for a period of 30 years, or 5 years after the most recent request, or for the effective life of the patent, whichever, is longer, and will be replaced if it ever becomes nonviable during that period. Additionally, with respect to Plant Variety Protection Certificates received and applied for, Applicant does not waive any infringement of its rights granted under this patent or under the Plant Variety Protection Act (7 U.S.C. 2312 et seq.).

What is claimed:

1. An inbred corn line designated NP 2045, the seeds of which have been deposited as ATCC Accession No. 209450.
2. A corn plant or parts thereof of inbred corn line designated NP 2045 of claim 1.
3. A corn plant having all the genetic, physiological and morphological characteristics of the plant of claim 2.
4. Seeds of the inbred corn line NP 2045 of claim 1.
5. Pollen of the inbred corn line NP 2045 of claim 1.
6. A tissue culture comprising regenerable cells of the plant according to claim 2.
7. A corn plant regenerated from the cells or protoplasts of a culture of corn tissue derived from and capable of expressing all the physiological and morphological characteristics of the corn plant of claim 3.
8. Hybrid seed produced by crossing plants of inbred corn line designated NP 2045, the seed having ATCC Accession No. 209450 and plants of another inbred corn line having a genotype different from corn line NP 2045.
9. Hybrid seed of claim 8 wherein the corn line NP 2045 is the male parent.
10. Hybrid corn plants grown from the seed of claim 8.
11. A tissue culture of regenerable cells of the corn plant of claim 10.
12. A first generation hybrid corn plant produced by growing hybrid corn seed, wherein said seed is produced by crossing a first inbred parent corn plant with a second inbred parent corn plant wherein said first or second inbred corn plant is the corn plant of claim 2 and harvesting the resultant hybrid seed.
13. Hybrid corn seeds produced by the process of:
    a) planting in pollinating proximity seeds of inbred corn line NP 2045 having ATCC Accession No. 209450 and a second inbred line having a genotype different from NP 2045;
    b) cultivating corn plants resulting from said planting until time of flowering;
    c) emasculating said flowers of plants of one of the corn inbred lines;
    d) allowing cross pollination to occur between said inbreds, and
    e) harvesting the seeds produced on said plants.
14. Hybrid corn plants produced by growing the seeds of claim 13.
15. A first generation (F1) hybrid corn plant produced by the process of:
    a) planting in pollinating proximity seeds of inbred corn line NP 2045 having ATCC Accession No. 209450 and a second inbred line having a genotype different from NP 2045;
    b) cultivating corn plants resulting from said planting until time of flowering;
    c) emasculating said flowers of plants of one of the corn inbred lines;
    d) allowing cross pollination to occur between said inbreds, and
    e) harvesting the seeds produced on said plants.
    f) growing a harvested seed of step e.
16. A corn plant regenerate from the cells or protoplasts of a culture of corn tissue and a genotype capable of expressing all the physiological and morphological characteristics of the corn plant of claim 15.

* * * * *